(12) United States Patent
Pickett et al.

(10) Patent No.: US 9,719,973 B2
(45) Date of Patent: Aug. 1, 2017

(54) SYSTEM AND METHOD FOR ANALYZING THE EFFECTIVENESS OF AN APPLICATION TO A CROP

(71) Applicant: Deere & Company, Moline, IL (US)

(72) Inventors: Terence D. Pickett, Waukee, IA (US); Timothy A. Wilcox, Cissna Park, IL (US)

(73) Assignee: DEERE & COMPANY, Moline, IL (US)

( * ) Notice: Subject to any disclaimer, the term of this patent is extended or adjusted under 35 U.S.C. 154(b) by 6 days.

(21) Appl. No.: 14/589,347

(22) Filed: Jan. 5, 2015

(65) Prior Publication Data

US 2016/0195505 A1    Jul. 7, 2016

(51) Int. Cl.
    *G01N 33/00* (2006.01)
(52) U.S. Cl.
    CPC .................. *G01N 33/0098* (2013.01)
(58) Field of Classification Search
    CPC .......................... G01N 33/0098; A01G 1/001
    USPC ............................................................ 702/2
    See application file for complete search history.

(56) References Cited

U.S. PATENT DOCUMENTS

| | | | |
|---|---|---|---|
| 4,015,366 A * | 4/1977 | Hall, III ............... | A01D 46/005 137/236.1 |
| 5,668,719 A * | 9/1997 | Bobrov ............... | A01M 7/0089 702/2 |
| 5,699,244 A * | 12/1997 | Clark, Jr. ............... | G06F 3/033 701/469 |
| 5,999,650 A * | 12/1999 | Ligon ................... | G06T 11/001 382/110 |
| 6,883,892 B2 | 4/2005 | Sievert | |
| 8,208,680 B2 | 6/2012 | Scharf | |

(Continued)

FOREIGN PATENT DOCUMENTS

| CN | 202953175 U | 5/2013 |
|---|---|---|
| CN | 203528823 U | 4/2014 |

(Continued)

OTHER PUBLICATIONS

Adamcuk, V., et al. Weed Targeting Herbicide Management. Precision Agriculture, University of Nebraska [online publication [retrieved on Jun. 1, 2015]. Retrieved from the Internet <URL:http://ianrpubs.unl.edu/live/ec708/build/ec708.pdf>.

(Continued)

*Primary Examiner* — Gregory J Toatley
*Assistant Examiner* — Douglas Kay

(57) ABSTRACT

In accordance with an example embodiment, a system is presented for collecting information about a crop to analyze the general health the crop relative to corresponding information from a previous information collection process. To ensure an optimal harvest, a field is typically treated with multiple material application steps. Starting with seed application, the system collects visual information and corresponding positioning data. With each subsequent application (e.g., fertilizer, pesticide, etc.), the information collection process is repeated. The new information is compared to corresponding information from a previous application step, such that the effectiveness of the prior application can be revealed.

16 Claims, 3 Drawing Sheets

(56) References Cited

U.S. PATENT DOCUMENTS

| | | | | |
|---|---|---|---|---|
| 8,319,165 | B2* | 11/2012 | Holland | A01B 79/005 250/206.1 |
| 8,594,897 | B2* | 11/2013 | Motavalli | G06Q 10/0631 111/200 |
| 8,831,292 | B2* | 9/2014 | Brueckner | G06K 9/34 382/110 |
| 8,897,973 | B2* | 11/2014 | Hunt | G06Q 10/00 701/1 |
| 9,076,105 | B2 | 7/2015 | Anderson | |
| 2001/0016053 | A1* | 8/2001 | Dickson | G01J 3/2803 382/110 |
| 2002/0022928 | A1* | 2/2002 | Ell | A01B 79/005 702/2 |
| 2003/0130767 | A1 | 7/2003 | Carroll | |
| 2005/0165552 | A1* | 7/2005 | Fraisse | A01B 49/06 702/2 |
| 2006/0106539 | A1* | 5/2006 | Choate | G06Q 10/10 702/2 |
| 2007/0019254 | A1 | 1/2007 | Zeng | |
| 2007/0091137 | A1 | 4/2007 | Lopez | |
| 2011/0313666 | A1* | 12/2011 | Hirvi | A01G 1/00 702/2 |
| 2012/0083907 | A1* | 4/2012 | Motavalli | G06Q 10/0631 700/90 |
| 2012/0195496 | A1 | 8/2012 | Zaman et al. | |
| 2014/0035752 | A1 | 2/2014 | Johnson | |
| 2014/0263822 | A1 | 9/2014 | Malveaux | |
| 2015/0371421 | A1* | 12/2015 | Hadfield | G09B 29/006 345/589 |

FOREIGN PATENT DOCUMENTS

| | | |
|---|---|---|
| DE | 4340096 A1 | 6/1994 |
| WO | 00/08590 A1 | 2/2000 |

OTHER PUBLICATIONS

Henry, W.B., et al. Remote Sensing to Distinguish Soybean from Weed After Herbicide Application. Weed Technology, vol. 18, Issue 3, Jul. 2004 [online], [retrieved on Jun. 1, 2015]. Retrieved from the Internet <URL: http://www.ars.usda.gov/SP2UserFiles/Place/30100000/2004Documents/2004/410%202004%20Henry%20Weed% 20Tech.pdf>.

Matthew J. Grassi. "New Hagie STS Sprayer Features AirScout Percision Package." CropLife, Jul. 8, 2015 [online] [Retrieved on Jul. 21, 2015]. Retrieved from the Internet: <http://www.croplife.com/equiptment/new-hagie-sts-sprayer-features-airscout-percision-package/>.

Simone Graeff, et al. "Evaluation of Image Analysis to Determine the N-Fertilizer Demand of Broccoli Plants." Hindawi Publishing Corporation, 2008. Advances in Optical Technologies, vol. 2008, 8 pages. <DOI:10.1155/2008/359760>.

Unpublished U.S. Appl. No. 14/813,573, filed Jul. 30, 2015 (53 pages).

Search Report issued in counterpart application No. GB1600139.8, dated Jun. 17, 2016 (4 pages).

\* cited by examiner

SYSTEM AND METHOD FOR ANALYZING THE EFFECTIVENESS OF AN APPLICATION TO A CROP

TECHNICAL FIELD

The system and method facilitates analyzing the effectiveness (e.g., efficacy) of a crop application of a substance to an agricultural field or crop. More specifically, the system facilitates an analysis showing changes to a crop over time that may be attributed to an application of a material or substance.

BACKGROUND

In certain prior art, the time between cultivation and harvest, treatments (e.g., fertilizers, pesticides, herbicides, etc.) are often applied to crops at intervals and quantities that are largely based on the farmer's real-time observations and past experience. A "trial-and-error" methodology for decision making is by no means optimal, but farming knowledge gained from prior experience can be a fairly reliable, yet not optimal predictor of a treatment's effectiveness on aspects of crop health.

Accordingly, there is a need for an automated system for assessing the effectiveness of crop treatment, such as an automated system that can be retrofitted to existing machinery with minimal investment of money and time. Operation of the system should require minimal human intervention.

SUMMARY

More specifically, this disclosure includes a method for assessing the effectiveness of an agricultural application that is executed by a computing system processing unit having a microprocessor. The method includes receiving sensor data and crop application parameters for crop at a particular location or a particular zone within a field and storing the data and parameters to a data storage device (e.g., database) as present crop data, wherein the present crop data includes a formatted subset of the sensor data and the crop application parameters. The processing unit invokes a search of the data storage device to locate prior crop data corresponding to a search parameter selected from the present crop data and corresponding to an agricultural application for the crop at the particular location or the particular zone. When prior crop data is located, the processing unit retrieves it from the data storage device. An analysis is performed to determine the effectiveness of the agricultural application, wherein the analysis includes a comparison of a first subset of the present crop data to a second subset of the prior crop data

BRIEF DESCRIPTION OF EXEMPLARY DRAWINGS

A more complete understanding of the present invention may be derived by referring to the detailed description and claims when considered in connection with the Figures, wherein like reference numbers refer to similar elements throughout the Figures, and:

DETAILED DESCRIPTION OF EXEMPLARY EMBODIMENTS

Figure 1:
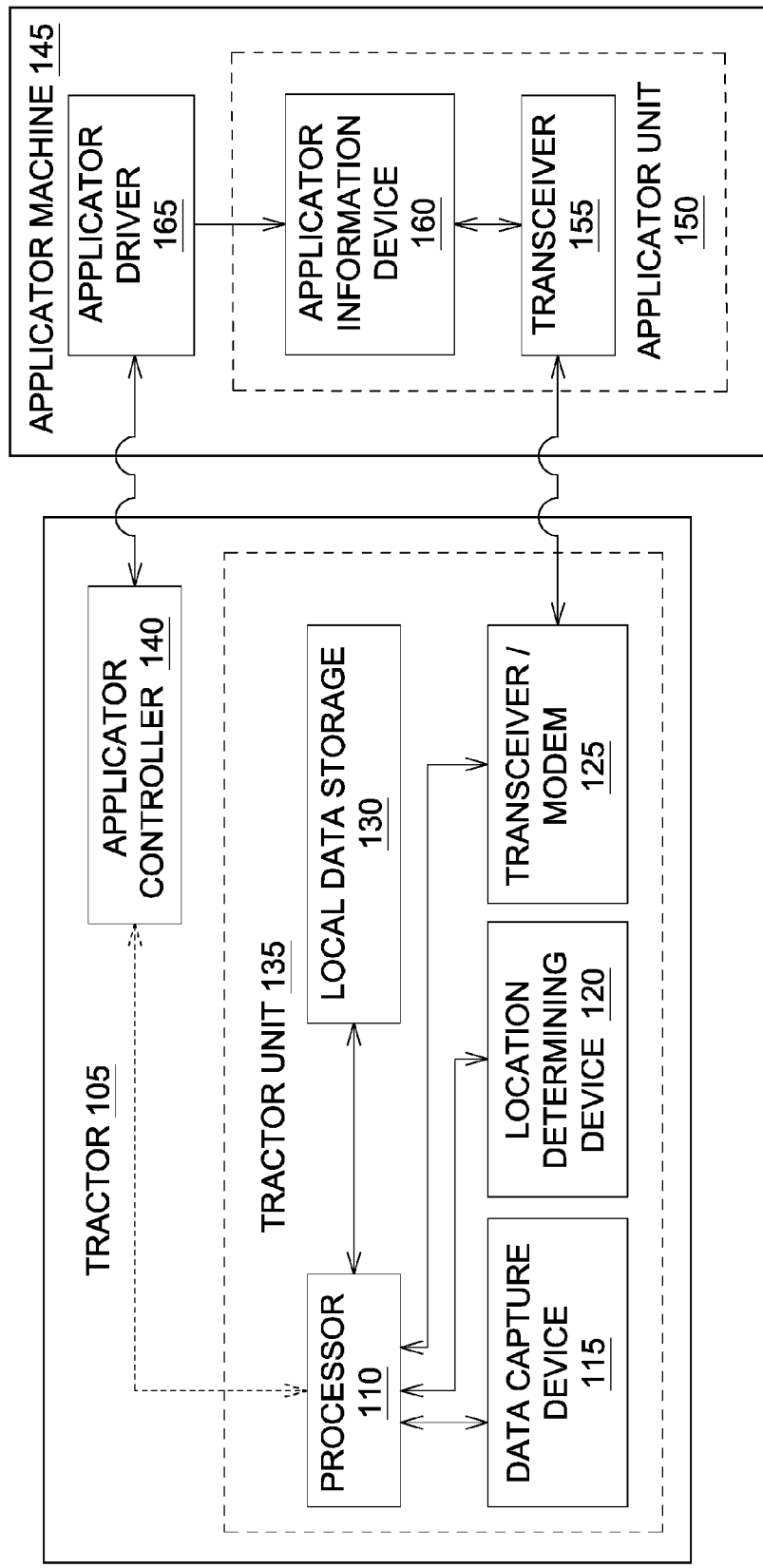
FIG. 1 is an enclosed system diagram including major hardware and software components for facilitating data collection and analysis in accordance with one embodiment.

In general, disclosed is a unique sampling and analysis processes for determining changes in a crop. The system invokes methods to determine by way of analysis whether detected crop changes may be attributed to a prior crop application. Attributes for a subsequent application may be determined in light of the analysis to increase the probability optimal results. In one embodiment, a confidence level for achieving favorable results based on a crop application increases relative to the number of related samples that are available for a cumulative analysis. Having multiple connected datasets, the system is able to facilitate a more precise analysis.

More specifically, the present system and methods enable applicator machinery to optimally apply (or not apply) calculated quantities of a substance or material to a field or crop as it moves about the field or crop. More specifically, the system comprises a means for creating a second image from an optical sensor, the image representing the present physical attributes of a section of a field or crop. A first image, having similar geographical coordinates to those of the second image, is retrieved from a storage device. The first and second images are processed in accordance with one or more comparison algorithms to identify points of differentiation. Rules are used to identify and nullify points of differentiation that have a low probability of resulting from an application of a material or substance to the field or crop area represented in the image.

As used herein, the term, "application" refers to a disbursement of a treatment to an agricultural field or crop or a process of applying a material or substance to a field or an agricultural crop (i.e., verb form) or may refer to the material or substance that has been or is to be applied (i.e., noun form). The mechanisms for performing an application may vary among embodiments and include, for example, spreading and spraying. In the context of this discussion, treated seed (e.g. chemically treated seed) qualifies as a treatment that is applied to a prepared soil bed by way of an application. An application may also include a process of dispersing fertilizer, pesticide, fungicide and the like to a field or crop by way of spraying or spreading, for example.

An "application" may also refer to the treated seed, fertilizer, or pesticide directly. The term "field" should be read in its broadest sense within the ordinary meaning. However, as primarily used herein, a field comprises a tillable or arable area of land that has been purposed for sustaining a crop.

A "crop" comprises a number of individual plants that have been cultivated within an area of a field; the crop being a direct result of an application of seed to a field. A seed or seedling application subsequently germinates to produce a crop of maturing agricultural product. In the context of this disclosure, a field would likely receive an application of seed, while a crop would most likely receive an application of fertilizer or pesticide.

Unless otherwise noted, the application process is facilitated by a specialized type of machinery, herein referred to as an "applicator." An applicator may include a drivable vehicle, such as a tractor that is equipped with a tank or container for holding the treatment. An applicator may also take the form of a towable or tow-behind that is configured to hold and apply seed, fertilizer, pesticide, etc. An applicator typically includes a number of controls that allow the operator to adjust, for example, the flow rate of the material to be applied to a field or crop. The flow or spread rate may be measured in terms of weight or volume of a substance that is applied to a field or crop within a measure of time.

Described herein as being a component of, or integrated within applicator machinery, an implementation of the system need not to be so limiting. The system, or components thereof, may be added to, or integrated within any other implement that may be typically used during crop cultivation and/or harvest. Moreover, the system may be implemented within specifically purposed machinery including drivable, pilotable, remote controlled and autonomous vehicles. For example, the system may be carried on or integrated within a remotely controlled or autonomous aerial drone.

In an autonomous vehicle embodiment, the vehicle may be controlled, driven, or piloted by an operator in real-time. The vehicle housing or carrying the system may also execute a program to traverse a defined path in a field or travel to specific locations to capture sensor (i.e., imaging) data. Accordingly, the vehicle and system may primarily function autonomously.

FIG. 1 is a system diagram including major hardware and software components for facilitating data collection and analysis in accordance with one embodiment. Those of ordinary skill in the art will appreciate that the components shown in FIG. 1 and discussed herein are presented for explanation only. The disclosed system may include any number of hardware and software components to optimally execute the disclosed methods. Ancillary hardware and software systems, which are known in the art but not material to the understanding of the disclosed system, will not be described beyond occasional mention. For example, most computer based systems implement at least minimal security restriction to protect the integrity of data. However, such systems and methods are well known and are outside of the scope of the disclosed system and methods and as such, will not be described in detail.

It is contemplated that the system 100 may be configured as standard or optional equipment by a manufacturer of agricultural farming machinery. It is further contemplated that the disclosed system hardware may be purchased as an aftermarket item or any other wholesale or retail environment where items specific to the farming industry are sold. In accordance with this configuration, the system 100 may be purchased as a kit, which includes all of the necessary hardware and software for self-installation. The system 100 may also be distributed as individual components, wherein various component configurations may be mixed and matched in accordance with the specific needs of the operator (i.e., "farmer").

The components shown in FIG. 1 function to overcome the limitations of the prior art by sampling, processing, and comparing sensor data to identify changes in the physical attributes of a field or crop for effecting an application. In one embodiment, the system 100 is integrated within the tractor 105 and/or applicator machine 145 during its manufacture or added as an aftermarket item. In another embodiment, the system 100 may be attachable and detachable, such that the operator is able to affix the tractor unit 135 to a component (e.g. bumper, mirror, window frame) of the tractor 105 by way of clamping, magnetics, suction, or any other non-permanent attachment means. Because the applicator unit 150 interfaces one or more applicator machine 145 microprocessors, such as an applicator information device 160, a more permanent integration is contemplated, but by no means necessary.

As used herein, an "applicator machine" 145 may comprise any agricultural machinery for applying a treatment to an area of soil or crop. An applicator machine 145 configured for cultivation may include, for example, a broadcast seeder, grain drill, planter, transplanter, fertilizer spreader, manure spreader, slurry spreader, sprayer, etc. An applicator machine 145 may further comprise machinery for treating a crop following cultivation and plant germination. An applicator machine 145 may be configured to disperse, for example, various types of solid fertilizers and further configured to disperse a liquid, such as a sprayer for applying pesticides.

In one embodiment, the applicator machine 145 is towed behind or attached to a tractor 105 or similar (i.e., trailed). Accordingly, the system 100 is illustrated and described in the context of two separate units (i.e., tractor unit 135 and applicator unit 150). However, it is contemplated that the system 100 may take the form of an integrated singular unit (i.e., drivable sprayer) where the applicator machine 145 and the tractor 105 are permanently combined.

An applicator machine 145 typically include at least one applicator controller 140 that allows an operator in the tractor 105 to adjust various properties of the applicator driver 165 without leaving the tractor 105 controls. For example, the applicator controller 140 allows the operator to start an application, stop an application, modify the flow or application rate, adjust the application area, view the level of remaining application, and the like. The applicator controller 140 may be wired to an applicator driver 165 within the applicator machine 145. In another embodiment, communication signals may be exchanged between the applicator controller 140 and applicator driver 165 by way of a wireless connection (e.g., BLUETOOTH® wireless connection, BLUETOOTH® low energy (BLE) connection, WI-FI® wireless connection, where BLUETOOTH® is a registered trademark of BLUETOOTH SIG, INC of Kirkland, Wash. and where WI-FI® is a registered trademark of the WIRELESS ETHERNET COMPATIBILITY ALLICANCE, INC. of Austin, Tex.).

In one embodiment, the tractor unit 135 is integrated with the applicator controller 140, such that an additional interface is not required to implement system 100. In another embodiment, tractor unit 135 utilizes the applicator controller as a backend device to provide the link with the applicator driver for sending commands and receiving status related information. In accordance with this embodiment, the tractor unit 135 may include an interface that allows the tractor 105 operator to view settings and status information and modify parameters as described herein.

In one embodiment, tractor unit 135 includes a small touchscreen display. In another embodiment, tractor unit 135 may be configured by way of a personal computer that either communicated parameters to the device by wired connection, BLUETOOTH® connection, WI-FI® connection, or Internet. In accordance with an Internet embodiment, the operator may access a web site and sign in using credentials. If an account has been setup, the IP for system 100 is stored along with the user's setup information. By way of a cloud application, the operator may enter or select from a map, coordinates that the operator would like the tractor unit 135 to sample.

In another embodiment, the tractor unit 135 includes a simple interface that provides a means for the operator to select the frequency for data capture. Data capture frequency may be in terms of number of captures within a timeframe. In another embodiment, the tractor unit 135 may invoke capture events at defined distance intervals. For example, the processor 110 may be configured to invoke a data capture device 115 every 50 feet of travel. In still another embodiment, the processor 110 may be configured to invoke the data capture device 115 to capture data when an application driver 165 sends signals to applicator machine 145 components to start or stop an application process.

In one embodiment, data capture device 115 records physical attributes of a crop as digitized images from a CCD or CMOS sensor. By way of optical comparison algorithms, transformations in a second image sample relative to a first image sample are measured and weighed against matrices to conclude with some certainty, that such transformations may be attributed, at least in part, to a prior application. Furthermore, in accordance with defined matrices, individual transformations may be classified having a value ranging from highly desirable to highly undesirable.

Figure 2:
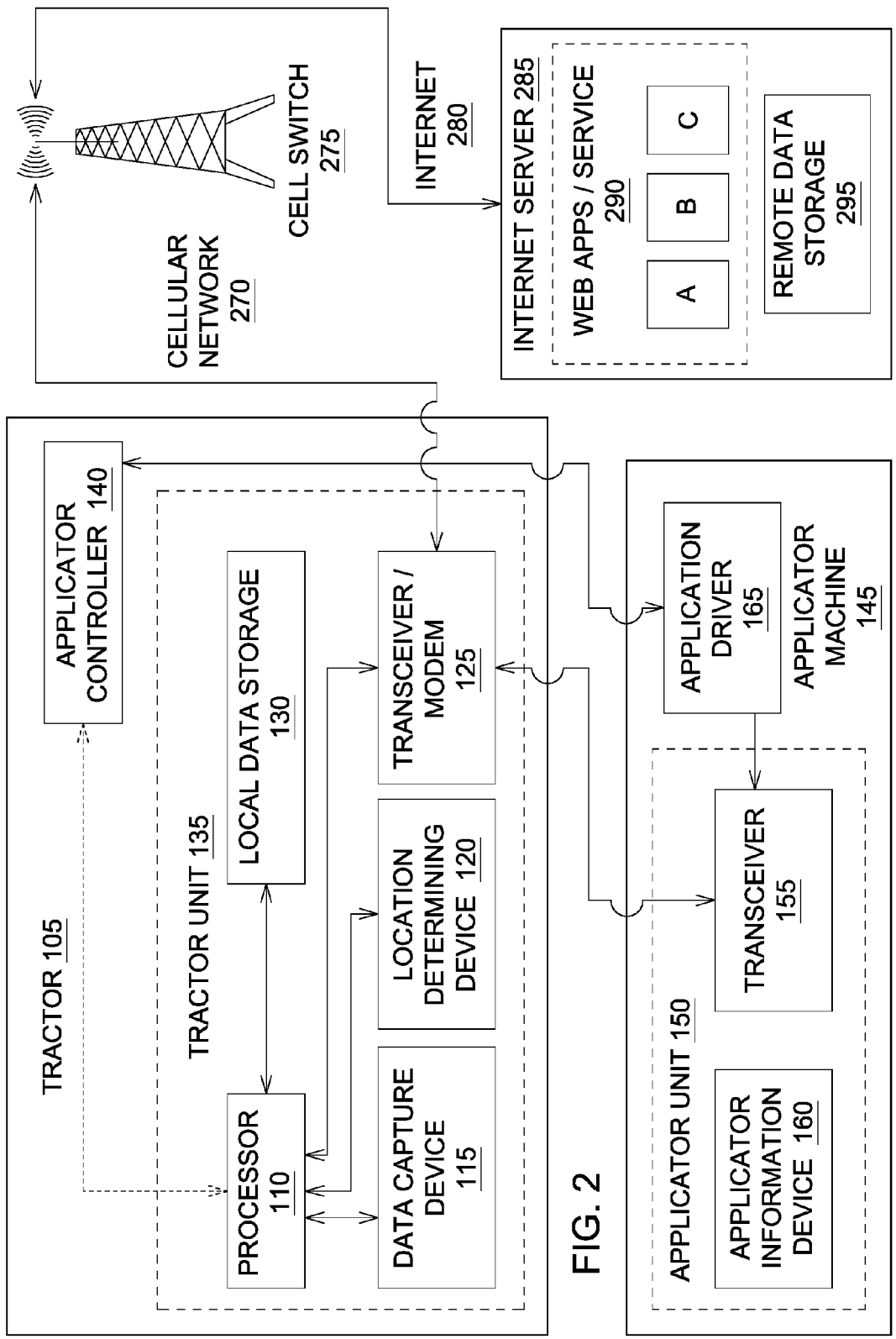
FIG. 2 is an Internet connected system diagram including major hardware and software components for facilitating data collection and analysis in accordance with one embodiment.

FIG. 2 is an Internet connected system diagram including major hardware and software components for facilitating data collection and analysis in accordance with one embodiment. While a full-time or permanent connection to a network or Internet is not a requirement, the embodiment presented in FIG. 2 benefits from having at least periodic connectivity to a remote data storage device 295, Internet server 285, and web applications/services 290.

The systems described relative to FIG. 1 and FIG. 2 are independently presented to simplify explanation. Those of ordinary skill in the art will appreciate that the system 100 may incorporate a subset of components from each of the presented embodiments. The system 100 may be configured to function in both "online" and "offline" modes utilizing, for example, the components necessary for wireless connectivity when operating within range of a wireless network 270 and a local data storage device 130 when operating outside of the range of a wireless network 270.

In one embodiment, the system 100 comprises a first subset of components that are positioned within a tractor 105 and a second subset of components that are positioned within an applicator machine 145. Each component subset may be integrated within the tractor 105 and/or applicator machine 145 during manufacture or added as aftermarket items. Moreover, the system 100 may be portable and able to be quickly added to and removed from a first tractor 105 and applicator unit 150 and subsequently added to a second tractor and applicator unit.

In one embodiment, the system 100 or a subset of system components are encased in one or more portable units. Accordingly, the tractor unit 135 or a portion thereof may be implemented within an existing personal communications device, such as a smartphone. The portable unit(s) may be in the possession of the operator who positions the unit(s) within the tractor 105 and/or applicator machine 145 prior to operation. Because the applicator unit 150 tightly interfaces the applicator driver 165, a more permanent integration is contemplated, but by no means necessary.

Communication between the tractor unit 135 and the applicator unit 150 may be facilitated by way of a wireless or wireline communication medium. In one embodiment, BLUETOOTH® Low Energy (BLE) provides a wireless platform for facilitating two-way data communications between the two units, or among individual components therein. However, those of ordinary skill in the art will appreciate that any wireless communication/networking protocol may be implemented to provide a communication link between components within each of the tractor unit 135 and the applicator unit 150 without departing from the scope of the invention.

Regardless of the selected communication medium implementation, the tractor unit 135, the applicator unit 150, or both, include one or more modem/transceivers (125, 155). Each one of the modem transceivers (125, 155) includes requisite hardware and software for performing various types of data communication tasks, including short range communication between the tractor unit 135 and the applicator unit 150. The data communication tasks may also include long range communication between either or both of the tractor unit 135 and/or applicator unit 150 and one or more distally located computing units (i.e. Internet server 285).

In one embodiment, the tractor unit 135 functions as the primary unit. The primary unit may be configured to communicate with the applicator unit 150 as well as to facilitate communications among various components of the system 100 (including both the tractor unit 135 and the applicator unit 150) and one or more Internet servers 285. In accordance with this embodiment, data transmission and reception between the transceiver/modem 125 and an Internet server 285 is wireless.

In one embodiment, a cellular modem within the transceiver/modem 125 establishes a connection with an Internet server 285 by way of a cellular network 270. When data is received at a cellular switching station 275 or similar, the data is formatted and routed over the Internet 280 to a designated Internet server 285. Likewise, data originating at the Internet server 285 is transmitted to the cellular switch 275 by way of the Internet 280. The data is formatted as required and sent over a cellular network 270 where it is received by the transceiver/modem 125.

The data flow as shown and described relevant to FIG. 2 is simplified in order to provide a general understanding of how the system 100 communicates internally and externally without detailing hardware, networks, protocols, encryption/decryption methods, compression algorithms, and other complexities associated with such an exchange of network data. Those of ordinary skill in the art will appreciate that a pathway connecting a transceiver/modem 125 to an Internet server 285 may include anywhere from one to dozens of physical interconnects, each having any number of methodologies and protocols for formatting and processing network data. An understanding of the disclosed system 100 does not require a detailed understanding of network data processing and no further description will be provided herein. Practitioners will appreciate that a thorough explanation of known data network methodologies and systems is not required and the absence of such detail does not limit the scope of the invention in any way.

In one embodiment, information that is collected by the data capture device 115 (e.g., digitizing camera), a location determining device 120, and/or any other system 100 component is transmitted to a cellular network 270 by the transceiver/modem 125. The information may traverse any number of public or private networks before being received by a designated server 285. Likewise, information from the Internet server 285 that is destined for the tractor unit 135 may traverse the same path of public and/or private networks or the information may be delivered to the destination tractor unit 135 through a disparate network path or combination of networks.

In one embodiment, information that is received by the Internet server 285 may be processed in accordance with a request, which is a part of the transmitted information. A request may include instructions for storing accompanying data within a remote data storage device 295, which is located with the Internet server 285 or is located with any other server residing on the same network or a connected network. Information that is to be stored in the remote data storage device 295 may include, for example, an operator identifier, a tractor unit 135 identifier, a applicator unit 150 identifier, a timestamp, location coordinates, environmental information (e.g., temperature, humidity, etc.), image data, application type identifier, application identifier, and the like.

Additional requests that are parsed from received information may include a processing request and information request. A processing request is parsed by the server 285 to determine the type of processing to be performed and to identify web applications or services 290 that may be called to optimally process the data in a manner that is consistent with the request. Web applications or services 290 may reside within a memory structure of the Internet server 285 or may be located at any other server residing on the same network or connected network. Web applications or services 290, for example, may be deployed by any third party to perform very specific operations in exchange for a use fee or subscription fee.

In one embodiment, web applications or services 290 may be called in response to an information storage request to augment or add specificity to information prior to storing it. For example, information including a storage request may be received by the Internet server 285 in response to a data collection process performed by the tractor unit 135. The information may include crop application data (e.g., material, application rate, etc.) from the applicator unit 150, coordinates as provided by a location service, and a timestamp but may not include other desired information such as environmental conditions. The Internet server 285, parses the request, determines the desired information to be stored, determines the types of included information, and identifies appropriate web applications or services 290 based on the desired information and the available information types. The Internet server 285 provides the identified parameters to web applications or services 290. The parameters might include the coordinates and timestamp. The web applications or services 290 use the coordinates and timestamp parameters to retrieve temperature and humidity data from a weather data storage device. The web applications or services 290 sends the results to the Internet server 285, the Internet server 285 adds the weather related data to the information received from the tractor unit 135, and stores the entire information packet to the remote data storage device 295.

As described herein, information originating from both the tractor unit 135 and the applicator unit 150 are formatted and transmitted to an external network by way of a modem/transceiver 125, which is a component of the tractor unit 135. In another embodiment, the applicator unit 150 serves as the primary information manager and the transceiver 155 functions in the manner described above in reference to the modem/transceiver 125. In yet another embodiment, the tractor unit 135 and the applicator unit 150 each include a modem/transceiver for communicating with an external network. As such, information may be transmitted and received by each of the units. Communication between the tractor unit 135 and the applicator unit 150 might be carried out by way of requests and responses that are sent and received over the external networks 270, 280.

In one embodiment, the features described relative to both FIG. 1 and FIG. 2 are combined into a third embodiment. In accordance with this third embodiment, the tractor unit 135 and/or applicator unit 150 includes one or more local data storage device systems 130 for storing information from the data capture device 115, applicator parameters, coordinates, environmental conditions, etc. The local data storage device 130 may have corresponding data storage device 295 that is periodically synchronized with information that is collected during offline operation.

With an ability to store information both locally 130 and remotely 295, the system is configured to function in both online and offline modes. Therefore, if a connection to a network 270, 280 is not available due to proximity or environmental factors, the system may continue to function normally by saving collected information locally. When access to an external network 270, 280 becomes available, the remote data storage device 295 may be synchronized with the information from the local data storage device 130.

Figure 3:
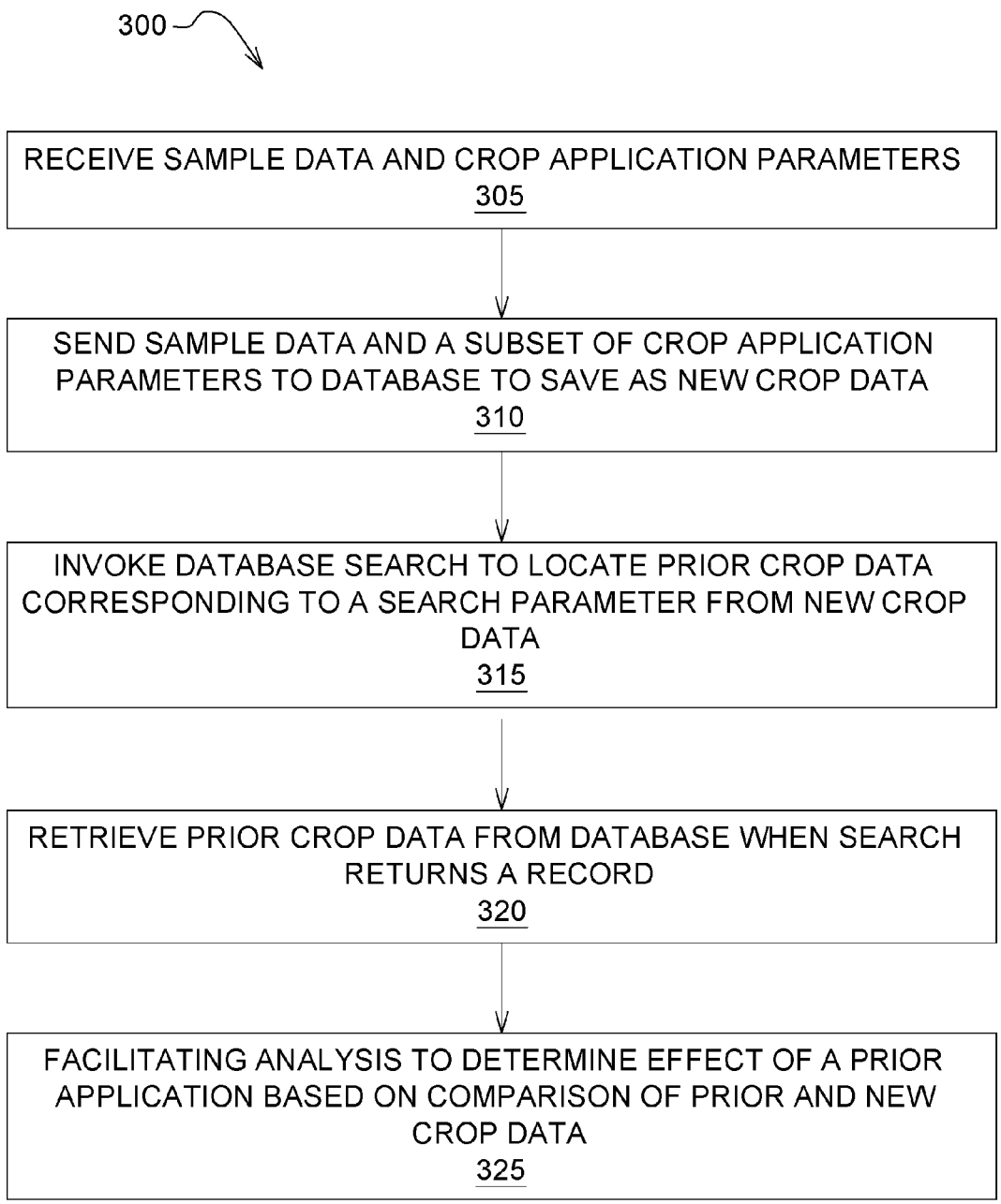
FIG. 3 is a process flow diagram outlining steps for executing the disclosed data collection and comparison method in accordance with one embodiment.

FIG. 3 is a process flow diagram outlining steps for executing the disclosed data collection and comparison method in accordance with one embodiment. Those of ordinary skill in the art will appreciate that the process steps shown and described may vary from one embodiment to another. The process may have steps that are executed in any order, include additional steps, or have fewer steps than those shown.

Moreover, although the system is described herein as comprising two distinct processing units (i.e., tractor unit 135 and applicator unit 150), this distinction will not be made in describing the processing steps. The physical location of the components providing the functions of the system 300 are not material to the unique features that each described component provides, both individually and collectively.

While in operation, the system 100 periodically receives data from the data capture device 115 and crop application parameters (step 305). The crop application parameters are received from an applicator driver 165 while a vehicle (i.e., tractor) with an attached applicator machine traverses a crop.

In one embodiment, an applicator machine 145 feeds the required data to an application controller 140 of the tractor 105 to allow the tractor operator to also monitor and control applicator machine 145 parameters. When this is the case, a preexisting connection between the applicator controller 140 and the applicator driver 165 is available. As such, application parameters may be received from the applicator controller 140, rather than requiring a second connection to the applicator driver 165.

In one embodiment, the crop application parameters include an application identifier. An application identifier is a unique descriptor of the material or substance that is disbursed onto a field or crop by the applicator machine 145. For example, and application identifier may simply indicate that the application is a "herbicide." However, an identifier will likely include more information that will further differentiate the application substance from other similar applications. Differentiating information may include an associated serial number, a trade name of the application, an application composition, and the like.

In one embodiment, crop application parameters include application rate and coverage area. The crop application parameters are most often set by the operator and in light of manufacturer indications and instructions. A number of variables may further influence decision making relative to setting and/or modifying application parameters. Such decision making is based, at least in part, on the operator's prior experience with the application. Prior experience (i.e., how did this application previously effect the crop?) is combined with the operator's observations of the present state of the crop to determine an optimal application parameters.

In one embodiment, the data generated by the capture device 115 comprises a numeric representation of a two-dimensional image. An image in digitized form is made up of a long series of numbers from which a microprocessor is able to reconstruct a two-dimensional representation of the image, one pixel at a time. However, because microprocessors are math based, the numeric representation allows computer systems to perform complex operations such as image modification, image comparison, and detecting and identify very slight variations between two or more images.

In one embodiment, the data from the capture device 115 comprises a digital image. As noted herein, a microprocessor processes and stores image data as a numeric representation. An image may take a number of forms including, for example, a thermal image, infrared image, or a NDVI (Normalized Difference Vegetation Index) image. Although significant differences between the image types exists, the various image types and formats are also processed and stored as numeric representations.

The NDVI is a graphical indicator that can be used to analyze remote sensing measurements, typically but not necessarily from a space platform, and assess whether the target being observed contains live green vegetation or not. Therefore, while NDVI is mentioned is the same context as other information that is collected by the data capture device 115, NDVI would more likely be captured during the later described process of collecting additional related information from a server or web applications/services.

Digitized images typically require a level of computer processing in order to be observable by a human. However, some imaging technologies capture information about an imaged subject beyond what is naturally observable by the human operator. As such, mathematical algorithms are executed by microprocessors to construct a visible representation of an image and the normally invisible information that a CCD or CMOS sensor is able to capture. For example, a digital thermal image is based on the amount of infrared energy emitted, transmitted, and reflected by an object. Although infrared energy is invisible to the human eye, a microprocessor is able to perform algorithms to interpret infrared data and build an image.

In one embodiment, the crop application parameters are received based on a data capture event. The data capture event is invoked by at least one of: operator action, a predefined time, a predefined time interval, coordinates of an applicator machine 145, predefined coordinates, and position of an applicator machine 145. A data capture event is detected by the processor 110 and may be based on input or data retrieved from the location determining device 120, local data storage device 130, remote data storage device 295, or any other component of system 100.

When a data capture event is detected, the processor 110 signals the data capture device 115 to invoke one or more sensors to capture data relating to the present state of a section of a field or crop. The data capture device 115 may include any number and type of sensors that are able to provide information useful in determining the general status, state, and/or health of a sampled geographical area. However, in the context of this disclosure, the data capture device 115 includes image sensors, such as CCD and CMOS sensors.

Following a data capture event, capture data is saved to either the local data storage device 130 or remote data storage device 295. In one embodiment, the capture data includes a formatted subset of information from the data capture device 115 and the crop application parameters (step 310). The crop application parameters, including a location identifier from the location determining device 120, are recorded to chronologically match the data capture event. In other words, recorded information relating to the application type, application disbursement rate, and geographic coordinates represent the moment in time when the data capture (e.g., photo) event occurred. In one embodiment, the dispersing rate is determined in light of the travel speed of the application machine 145.

Following two or more application processes to a single field or crop, an operator or any other authorized user is able to invoke an analysis of the application affects. Based on either an operator's action or in response to a request from a program and/or system, a search of the local data storage device 130 and/or remote data storage device 295 locates prior crop data corresponding to a search parameter selected from the present crop data (step 315). In one embodiment, the search parameter includes a unique location identifier captured from the location determining device and stored with the capture data.

When one or more record matching the search parameter is located, data from the located one or more records is retrieved (step 320). The located one or more records each represent data captured during a prior application processes. In one embodiment, returned record data is formatted in accordance with a selected analysis type. For example, if the analysis is to be performed by a third-party computer program, then the returned data is formatted in accordance with the requirements of the target program. However, if the analysis is to be performed by a human operator, then the returned data may be organized into a report format in accordance with the operator's defined preferences.

Whether performed by way of a computing system, human observation and calculation, or a combination thereof; system 100 facilitates an analysis process to determine an effectiveness of the agricultural application based on a comparison of a first selected set of crop data to a second selected set of crop data (step 325).

In one embodiment, an automated or semi-automated analysis may comprise a pixel-level comparison of a first digitized image to a second digitized image. For example, when images during the subsequent passes are captured from the same location, angle, general lighting conditions, etc., a number of variations between the images can be detected by counting the number of pixels within a given area of an image and determining the precise color for each pixel. Color differentiation may be used to distinguish plant matter from other environmental and background elements (e.g., soil and sky).

Also, the general health of an agricultural plant or a weed may be determined by way of color differentiation process between an image element from a first image and an image element of a second image, when each image occupies the same general coordinates. For example, a first crop image may include a group of plants that are identified as being healthy due to the number of green pixels occupying certain image coordinates. Following an application of a herbicide to the crop, a second image may contain brown pixels within the same image coordinates. Such an analysis may be a strong indicator that the herbicide application was effective in killing weeds within the crop.

Those of ordinary skill in the art will appreciate that an analysis may consider any number of crop data records, where each record represents a different data capture event for a single crop or area of crop. The system 100 may incorporate proprietary methods for analyzing crop data or may utilize known crop metrics to determine the effectiveness of specific crop applications. NDVI (Normalized Difference Vegetative Index) is an example of one widely used crop metric relating to plant growth, plant appearance, and plant health. NDVI is based on differences in optical reflectivity of plants and dirt at different wavelengths.

In one embodiment, the system 100 facilitates computer assisted analysis of crop health over time using software models. In another embodiment, analysis may be performed, for example, in an office environment by an agronomist using the collected images and or other types of sensor data. The images may contain visual or non-visual elements to fully understand the effectiveness of one or more application procedures.

The system may be described herein in terms of functional block components, optional selections and/or various processing steps. It should be appreciated that such functional blocks may be realized by any number of hardware and/or software components suitably configured to perform the specified functions. For example, the system may employ various integrated circuit components such as, memory elements, processing elements, logic elements, look-up tables, and/or the like. The integrated circuit components may carry out a variety of functions under the control of one or more microprocessors or other control devices. Similarly, software elements may be implemented with any programming or scripting language with the various algorithms being implemented with any combination of data structures, objects, processes, routines or other programming elements.

As may be appreciated by one of ordinary skill in the art, the system may be embodied as a method, a data processing system, a device for data processing, a hardware controller, and/or a computer program product. Accordingly, the system may take the form of an entirely software embodiment, an entirely hardware embodiment, or an embodiment combining aspects of both software and hardware.

Computer program code may also be stored in a computer-readable memory that may direct a computer or other programmable data processing apparatus to function in a particular manner, such that the instructions stored in the computer-readable memory produce an article of manufacture including instruction means which implement functions of flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus include steps for implementing the functions specified in the description.

In the foregoing specification, the system has been described with reference to specific embodiments. However, it may be appreciated that various modifications and changes may be made without departing from the scope of the invention. The specification and figures are to be regarded in an illustrative manner, rather than a restrictive one, and all such modifications are intended to be included within the scope of invention. Accordingly, the scope of the invention should be determined by the appended claims and their legal equivalents, rather than by the examples given above. For example, the steps recited in any of the method or process claims may be executed in any order and are not limited to the order presented.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical."

What is claimed is:

1. A method for assessing the effectiveness of an agricultural application, the method comprising:
   capturing, by a data capture device associated with a ground vehicle, sensor data that comprises image data of a crop at a particular location or a particular zone within a field;
   determining, by a location-determining device, the particular location or a location identifier;
   receiving, at a processing unit, the sensor data and crop application parameters for the crop at the particular location or the particular zone within the field, wherein present crop data comprises the received sensor data and crop application parameters;
   storing, by the processing unit, prior crop data in a data storage device, prior crop data comprising a subset of the sensor data and the crop application parameters;
   searching, by the processing unit, the data storage device to locate the stored prior crop data corresponding to the present crop data and corresponding to an agricultural application for the crop at the particular location or the particular zone;
   retrieving, by the processing unit, the prior crop data from the data storage device; and
   facilitating, by the processing unit, an analysis to determine the effectiveness of the agricultural application with respect to plant growth, plant health or killing weeds within the crop, wherein the analysis includes a comparison by pixel color of green and brown pixels of the image data of the present crop data to the prior crop data to determine variation between present and prior images within a given area of the images, wherein the comparison comprises counting pixels within the given area of the collected image data and distinguishing the pixels according to pixel color by color differentiation, the pixels from the particular location or the particular zone of the present crop data compared against the same particular location or the same particular zone of the prior crop data, and wherein the image data of present crop data and prior crop data are captured from the same locations and same angles during passes of the vehicle to collect the image data.

2. The method of claim 1, wherein the counting produces properties relating to plant height, leaf size, plant type, and plant health.

3. The method of claim 1, wherein at least one of: the sensor data and the crop application parameters are received from an applicator machine.

4. The method of claim 1, wherein the crop application parameters include an application identifier.

5. The method of claim 1, wherein the crop application parameters include application rate and coverage area.

6. The method of claim 1, wherein the sensor data comprises a numeric representation of a two-dimensional image.

7. The method of claim 1, wherein the sensor data comprises at least one of: a digital image, a thermal image, infrared image, and a NDVI (Normalized Difference Vegetation Index) image.

8. The method of claim 1, wherein the prior application data includes information relating to a plurality of prior applications.

9. The method of claim 1, wherein the crop application parameters are received based on a data capture event.

10. The method of claim 9, wherein the data capture event is invoked by at least one of: operator action, a predefined time, a predefined time interval, coordinates of an applicator machine, predefined coordinates, and position of an applicator machine.

11. The method of claim 1, wherein the effectiveness of the agricultural application includes a metric relating to at least one of: plant growth, plant appearance, and plant health.

12. The method of claim 1, wherein at least one of: the processing unit and the storage device is implemented within at least one of: an applicator machine, a drivable vehicle, a pilotable vehicle, a remotely controlled vehicle and an autonomous vehicle.

13. The method of claim 1, wherein the crop application parameters include location data.

14. The method of claim 13, wherein the search parameter is a unique location identifier retrieved from the location data.

15. The method of claim 13, wherein the location data is received from a satellite location system.

16. A method for assessing the effectiveness of an agricultural application of a herbicide, the method comprising:
    capturing, by a data capture device associated with a ground vehicle, sensor data that comprises image data of a crop at a particular location or a particular zone within a field;
    determining, by a location-determining device, the particular location or a location identifier;
    receiving, at a processing unit, the sensor data and crop application parameters for the crop at the particular location or the particular zone within the field, wherein present crop data comprises the received sensor data and crop application parameters;
    storing, by the processing unit, prior crop data in a data storage device, prior crop data comprising a formatted subset of the sensor data and the crop application parameters;
    searching, by the processing unit, the data storage device to locate the stored prior crop data corresponding to the present crop data and corresponding to an agricultural application for the crop at the particular location or the particular zone;
    retrieving, by the processing unit, the prior crop data from the data storage device; and
    facilitating, by the processing unit, an analysis to determine the effectiveness of the agricultural application with respect to plant health or killing weeds within the crop, wherein the analysis includes a comparison by pixel color of green and brown pixels of the image data of the present crop data to the prior crop data to determine variation between present and prior images within a given area of the images, wherein the general health of an agricultural plant or a weed may be determined by way of color differentiation process between an image element from a first image and an image element of a second image, when each image occupies the same general coordinates, and where a first image may include a group of plants that are identified as being healthy due to the number of green pixels occupying certain image coordinates, and a second image may contain brown pixels within the same image coordinates indicative that the application of the herbicide was effective in killing weeds within the crop.

\* \* \* \* \*